United States Patent [19]

Weiner et al.

[11] Patent Number: 5,376,381
[45] Date of Patent: Dec. 27, 1994

[54] INTEGRITY PROTECTED GELATIN

[75] Inventors: Alan L. Weiner, Lawrenceville, N.J.; Joel B. Portnoff, Richboro; Elaine Chan, Feasterville, both of Pa.

[73] Assignee: The Liposome Company, Inc., Princeton, N.J.

[21] Appl. No.: 649,237

[22] Filed: Jan. 29, 1991

Related U.S. Application Data

[63] Continuation of Ser. No. 241,906, Sep. 7, 1988, abandoned, which is a continuation-in-part of Ser. No. 160,141, Feb. 25, 1988, Pat. No. 5,154,930.

[51] Int. Cl.$^5$ .......................... A61K 9/48; A61K 9/64; A61K 9/66; B01J 13/02
[52] U.S. Cl. ................................... 424/456; 424/452; 424/455; 424/492; 428/402.2; 514/962
[58] Field of Search .................. 428/402.2; 424/452, 424/455, 456, 492; 514/962; 206/828

[56] References Cited

U.S. PATENT DOCUMENTS

| | | | |
|---|---|---|---|
| 160,141 | 2/1888 | Popescu et al. | |
| 2,780,355 | 2/1957 | Palermo et al. | 424/452 |
| 4,438,052 | 3/1984 | Weder et al. | 264/4.6 |
| 4,497,157 | 2/1985 | Durr et al. | 53/428 |
| 4,567,161 | 1/1986 | Posanski et al. | 514/23 |
| 4,687,766 | 8/1987 | Wendel et al. | 514/78 |
| 4,708,834 | 11/1987 | Cohen et al. | 264/4.3 |
| 4,842,865 | 6/1989 | Durr et al. | 424/456 |
| 4,844,926 | 7/1989 | Hatanaka | 426/614 X |

FOREIGN PATENT DOCUMENTS

| | | |
|---|---|---|
| 0100052 | 8/1984 | European Pat. Off. |
| 0056315 | 5/1978 | Japan ................................. 514/78 |
| 0163819 | 8/1985 | Japan ................................. 424/452 |
| 1008044 | 10/1965 | United Kingdom . |
| 2155789A | 10/1985 | United Kingdom . |

OTHER PUBLICATIONS

Webster's Ninth New Collegiate Dictionary, 1984, p. 81.
Remington's *Pharmaceutic Sciences*, 15th Edition (1975), Mack Publishing Co., Easton, PA, pp. 422–425 & 437.
Lachman, et al., The Theory and Practice of Industrial Pharmacy, 3rd Ed. p. 402 (1986).

*Primary Examiner*—Richard D. Lovering
*Attorney, Agent, or Firm*—Joanne Longo Feeney

[57] ABSTRACT

A pharmaceutical dosage form comprising gelatin encapsulating a pharmaceutical composition wherein said composition is at least about 6% (weight %) ethanol and lipid wherein said lipid comprises at least about 60% (weight %) and a method of protecting gelatin from deterioration is disclosed.

14 Claims, No Drawings

INTEGRITY PROTECTED GELATIN

This application is a continuation of Ser. No. 07/241,906 filed Sept. 7, 1988, now abandoned, which is a continuation-in-part of Ser. No. 07/160,141 filed Feb. 25, 1988, now U.S. Pat. No. 5,154,930.

FIELD OF THE INVENTION

This invention is concerned with a pharmaceutical dosage form comprising gelatin encapsulating a pharmaceutical composition wherein said composition is at least about 6% (weight %) ethanol and lipid wherein said lipid comprises at least about 60% (weight %) and a method of protecting gelatin from deterioration.

BACKGROUND OF THE INVENTION

The pharmaceutical art has long recognized the utility of gelatin as a "shell" material for the encapsulation of medicaments into a convenient dosage form. Gelatin is easily processed and may be colored with various pharmaceutically acceptable colorants. Gelatin is generally divided into Type A for acid extracted gelatin and Type B for base extracted gelatin. Combinations of gelatin are useful in this art. As used in the pharmaceutical art gelatin is prepared in a mixture with water and glycerin or other plasticizer to the desired flexibility. The amount of water and glycerin is frequently varied with a view to the desired final hardness of the shell. Commonly those skilled in the art use hard (0.4:1 glycerin to gelatin) for oral, oil-based, or shell softening products and those destined for hot humid climates, medium (0.6:1) for oral, tube, vaginal oil-based, water-miscible or shell-hardening products and those destined for temperate climates, and soft (0.8:1) for tube, vaginal, water-miscible based or shell-hardening products and those destined for cold dry areas. A draw back to the use of gelatin is its propensity deteriorate by drying out and cracking or becoming brittle.

Ethanol and other alcohols are well known pharmaceutical diluents, excipients and solvents used in compounding numerous dosage forms. Alcohol is also a drying agent and thus limited in its use with gelatin. It is generally understood that a gelatin preparation such as a gelatin capsule must be less than about 5% ethanol lest the ethanol dry the gelatin and cause unacceptable deterioration of the gelatin.

*The Theory and Practice of Industrial Pharmacy*, 3rd Ed., p402, Leon Lachman et al.; Lea & Febiger, Philadelphia (1986) states that water-miscible liquids which are also volatile cannot be major gelatin capsule constituents. Alcohol is specifically cited as such a constituent and about 5% of encapsulated material is stated to be the maximum amount.

Thus a very useful article would be a gelatin pharmaceutical dosage form that can encapsulate medicaments with over 5% ethanol and not deteriorate.

SUMMARY OF THE INVENTION

This invention includes a pharmaceutical dosage form comprising gelatin (including Types A and B) encapsulating a pharmaceutical composition wherein said composition is at least about 6% (weight %) ethanol and lipid wherein said lipid comprises at least about 60% (weight %). The dosage form can contain a bioactive agent.

The dosage form can be any form including a capsule, trochée, dragée, suppository or tablet adapted to pharmaceutical administration.

A preferred lipid of the dosage form is a phospholipid. In a preferred dosage form ethanol comprises from about 6% to about 15% by weight of said dosage form, more preferred being wherein the ethanol comprises from about 7% to about 15% by weight of said dosage form and yet more preferred wherein the ethanol comprises from about 7% to about 10% by weight of said dosage form and particularly from about 7% to about 8% by weight of said dosage form.

In a preferred dosage form the lipid comprises at least about 66% by weight of said dosage form, more preferred being wherein the lipid comprises at least about 75% by weight of said dosage form yet more preferred wherein the lipid comprises at least about 85% by weight of said dosage form and particularly about 94% by weight of said dosage form.

This invention also includes a method of preventing gelatin vesicle (including Types A and B) dosage forms containing from about 6% (weight %) ethanol from deterioration by the step of admixing at least about 60% (weight %) lipid with said ethanol. The method includes dosage forms that include a bioactive agent.

The method is applicable to a dosage form of any form including a capsule, trochée, dragée, suppository or tablet adapted to pharmaceutical administration.

In the practice of the method a preferred lipid of the dosage form is a phospholipid.

Furthermore in the practice of the method ethanol comprises from about 6% to about 15% by weight of the dosage form, more preferred being wherein the ethanol comprises from about 7% to about 15% by weight of the dosage form and yet more preferred wherein the ethanol comprises from about 7% to about 10% by weight of the dosage form and particularly from about 7% to about 8% by weight of the dosage form. About 8 to 10% ethanol is also included.

Additionally in the practice of the method the lipid comprises at least about 66% by weight of said dosage form, more preferred being wherein the lipid comprises at least about 75% by weight of said dosage form yet more preferred wherein the lipid comprises at least about 85% by weight of said dosage form and particularly about 94% by weight of said dosage form.

DETAILED DESCRIPTION OF THE INVENTION

The pharmaceutical dosage form of this invention possesses valuable pharmacological properties. It provides for amounts of the alcohol of at least about 6%, and in some embodiments of at least about 7, 10 or 15% or more in a stable gelatin configuration. Furthermore, increased alcohol permits solubilization of greater amounts of medicament in a particular formulation. All percentages herein are understood to be weight per cent unless otherwise stated. As referring to the contents of a pharmaceutical dosage form weight % refers to the dosage form contents and does not include the weight of encapsulating gelatin. A stable dosage form in a high alcohol content formulation can be a particular advantage in the field of human and veterinary medicine. Stable as to a pharmaceutical dosage form of a gelatin is well defined in the pharmaceutical art (e.g., U.S. Pharmacopeia XXI Ed., p1346 (U.S. Pharmacopeia Convention, Washington, D.C.)) and is understood to be no change in the gross physical appearance or consistency, including hardening or softening of the gelatin. Evidence of instability includes gas release, splits or cracks, separation (as to capsules), and dimpling. Stable as used herein further entails maintaining such condition for at least about three months and preferably for about one year and more preferably for about two years.

Gelatin of this invention includes both Types A and B used alone or in combination. Gelatins are available from such sources as R. P. Scherer Corp. (Troy, Mich.), and Eli Lilly (Indianapolis, Ind.).

Gelatin may be obtained in many forms including capsules, powders, beads, solutions or dispersions.

Plasticizers for admixture with the gelatin include gylcerin, triethylcitrate, dibutyl sebacate, propylene glycol and water.

Increased stability for the instant pharmaceutical dosage form is demonstrated by comparing the stability of soft gelatin capsules containing at least about 6% alcohol and further containing lipid to capsules identical but for the lipid. After about one week at 20°-25° C. in 75-80% humidity the capsules without lipid have become visibly cracked, leaky and brittle to the touch. Under identical conditions the lipid containing capsules are unchanged.

In various embodiments these pharmaceutical dosage forms can be used in the encapsulation of ethanol soluble drugs such as nonsteroidal anti-inflammatory drugs (e.g., indomethacin), sterotdal anti-inflammatory drugs, benzodiazepines, polyene antibiotics (e.g., amphotericin B), cephalosporins, and antifungals (e.g., miconazole).

In addition, the pharmaceutical dosage forms can be used in the unit dosage form.

Typical unit dosage forms are capsule sizes 000 through 5 which depending on capsule wall thickness are from about 0.1 ml to about 5 ml, however other sizes are well known in the art.

The pharmaceutical dosage forms of this invention are generally administered to animals, including but not limited to humans, livestock, household pets, cattle, cats, dogs, poultry, etc.

The pharmacologically active compositions of this invention can be processed in accordance with conventional methods of galenic pharmacy to produce medicinal agents for administration to patients, e.g., mammals including humans.

The compositions of this invention can be employed in admixture with conventional excipients, i.e., pharmaceutically acceptable organic or inorganic carrier substances suitable for parenteral or oral or suppository application. Suitable pharmaceutically acceptable carriers include but are not limited to lecithin, myglyol, vegetable oils, polyethylene glycols, silicone oils, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the gelatin. They can also be combined where desired with bioactive agents such as for example, a drug, hormone, protein, dye, vitamin, or imaging agent. As used in the present invention, the term bioactive agent is understood to include any compound having biological activity; e.g., drugs and other therapeutic agents such as peptides, hormones, toxins, enzymes, neurotransmitters, lipoprotetns, glycoproteins, immunomodulators, immunoglobulins, polysaccharides, cell receptor binding molecules, nucleic acids, polynucleotides, and the like, as well as including biological tracer substances such as dyes, radio-opaque agents, and fluorescent agents.

It will be appreciated that the actual preferred amounts of bioactive agents in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

Lipid materials used in this invention are amphipathic in character. Amphipathic as defined herein is a moiety with a hydrophobic portion and a hydrophilic portion. Hydrophilic character will be imparted to a molecule through the presence of phosphatidic, carboxylic, sulphatic, amino, sulfhydryl, nitro, and other groups such as carbohydrates. Hydrophobicity will be conferred by the inclusion of groups that include, but are not limited to, long straight and branched chain saturated and unsaturated aliphatic hydrocarbon groups and such groups substituted by one or more aromatic, cycloaliphatic or heterocyclic group. The preferred amphipathic compounds are phosphoglycerides, representative examples of which include phosphatidylcholines, phosphatidylethanolamines, lysophosphatidylcholines, lysophosphatidylethanoloamines, phosphatidylserines, phosphatidylinositols, phosphatidic acids, phosphatidylglycerols and diphosphatidylglycerols as well as sphingomyelins. Synthetic saturated compounds such as dimyristoylphosphatidyl-choline and dimyristoylphosphatidylglycerol or unsaturated species such as dioleoylphosphatidylcholine or dilinoleoylphosphatidylcholine are also usable. Other compounds lacking phosphorous, such as members of the glycolipids, and glycosphingolipid, ganglioside and cerebroside families, are also within the group designated as amphipathic lipids. Salts of acid derivatives of sterols and tocopherols such as cholesterol hemisuccinate or tocopherol hemisuccinate are also amphipathic. Salts of acid derivatives of sterols are further described in U.S. Pat. No. 4,721,612 to Janoff et al., the teachings of which are incorporated herein by reference. Ionic detergents such as octadecanylsulfonate are also included. Phospholipids are particularly preferred.

Lipids used in this invention are obtainable from a number of sources. Natural phosphatide mixtures from egg or soy containing more than 70% phosphatidylcholine are obtained from a number of commercial sources such as Sigma Chemical of St. Louis, Mo., and Lipold KG, Ludwigshafen, West Ger., Hepar of Franklin, Ohio. Hepar supplies egg phosphatidylcholine. Other sources of lipid such as soy phosphatidylcholine are American Lecithin, Woodside, L.I., N.Y., and Riceland Foods, Little Rock, Ark. Phosphatidic acid of 99% purity is obtained from Avanti Chemical of Birmingham, Ala.

The amount of lipid required will vary with the hardness of the gelatin capsule initially. Harder capsules will require somewhat more lipid for longest maintenance of capsule quality as compared to soft gelatin capsules. Further, as to the protective capability of different lipids, phospholipids are most preferred. In most instances at least about 60% (weight %) lipid is required, and preferably about 66% lipid or more. More preferred is at least about 75% lipid and yet more preferred is at least about 85% lipid. Depending on the lipid and method of preparing capsules about "94% lipid" as a maximum amount to avoid undue viscosity and attendant filling problems.

EXAMPLE 1

Indomethacin Preparation 15 g of egg phosphatides (Lipoid E80, Ltpoid KG, Ludwigshafen, West Ger.) containing 80% phosphatidylcholine was solubilized in 3 ml absolute ethanol. The resulting co-mixture then solubilized indomethacin, 1 g of which was then added to the co-mixture. The final preparation contained 25 mg of indomethacin and 375 mg of lipid per 0.4 ml and 0.075 ml per 0.4 ml ethanol (7% by weight). This procedure was performed at about 22.5° C.+/−about 2.5° C. at and atmospheric pressure. 0.4 ml of the preparation was encapsulated in a soft gelatin capsule as a unit oral dosage form. These gelatin capsules remained stable over three months post filling.

EXAMPLE 2

Gelatin Capsule Formulations

The following capsules were prepared using soft gelatin capsules:

| Lipid Weight % | Ethanol Weight % | Other Weight % |
| --- | --- | --- |
| 66 | 7 | 27 (miglyol) |
| 90 | 10 | — |
| 85 | 15 | — |
| 92.4 | 7.6 | — |

We claim:

1. A pharmaceutical dosage form comprising gelatin encapsulating a pharmaceutical composition wherein said composition comprises at least about 6% ethanol by weight and wherein said composition comprises at least about 60% phosphalipid by weight wherein said lipid comprises at leas about 60%.

2. The dosage form of claim 1 wherein the gelatin comprises Type A gelatin.

3. The dosage form of claim 1 wherein the gelatin comprises Type B gelatin.

4. The dosage form of claim 1 wherein said form is a capsule, trochée, dragée, suppository or tablet adapted to pharmaceutical administration.

5. The dosage form of claim 1 wherein said ethanol comprises from about 7% to about 15% by weight of said composition.

6. The dosage form of claim 1 wherein said phosphalipid comprises at least about 85% by weight of said composition.

7. The dosage form of claim 1 further comprising a bioactive agent.

8. A method of preventing deterioration of gelatin encapsulated dosage forms comprised of a pharmaceutical composition containing from about 6% ethanol by weight by the step of admixing at least about 60% phosphalipid by weight with said ethanol.

9. The method of claim 8 wherein the gelatin comprises Type A gelatin.

10. The method of claim 8 wherein the gelatin comprises Type B gelatin.

11. The method of claim 8 wherein said form is a capsule, trochée, dragée, suppository or tablet adapted to pharmaceutical administration.

12. The method of claim 8 wherein said ethanol comprises form about 7% to about 15% by weight of said composition.

13. The method of claim 8 wherein said phosphalipid comprises at least about 85% by weight of said composition.

14. The method of claim 8 wherein said dosage form further comprises a bioactive agent.

* * * * *